(12) United States Patent
Liu et al.

(10) Patent No.: US 7,963,697 B2
(45) Date of Patent: Jun. 21, 2011

(54) GAIN CALIBRATION AND CORRECTION TECHNIQUE FOR DIGITAL IMAGING SYSTEMS

(75) Inventors: James Zhengshe Liu, Glenview, IL (US); John Lamberty, Oconomowoc, WI (US); Ping Xue, Pewaukee, WI (US); Donald Langler, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 192 days.

(21) Appl. No.: 12/356,488

(22) Filed: Jan. 20, 2009

(65) Prior Publication Data

US 2010/0183124 A1    Jul. 22, 2010

(51) Int. Cl.
*H05G 1/26* (2006.01)
(52) U.S. Cl. .................................. 378/207; 378/98.8
(58) Field of Classification Search ............. 378/98.7, 378/98.8, 19, 207
See application file for complete search history.

(56) References Cited

U.S. PATENT DOCUMENTS

| | | | | |
|---|---|---|---|---|
| 5,452,338 | A | * | 9/1995 | Granfors et al. ........... 378/98.11 |
| 5,920,070 | A | * | 7/1999 | Petrick et al. ............... 378/98.8 |
| 6,393,098 | B1 | | 5/2002 | Albagli |
| 6,457,861 | B1 | | 10/2002 | Petrick et al. |
| 6,798,864 | B2 | | 9/2004 | Petrick et al. |
| 7,138,636 | B2 | | 11/2006 | Petrick et al. |
| 2003/0223539 | A1 | * | 12/2003 | Granfors et al. ............. 378/98.8 |
| 2006/0222146 | A1 | * | 10/2006 | Spahn ......................... 378/98.8 |

* cited by examiner

*Primary Examiner* — Chih-Cheng G Kao
(74) *Attorney, Agent, or Firm* — Fletcher Yoder P.C.

(57) ABSTRACT

A gain correction and calibration technique for digital imaging systems is provided. In one embodiment, a method may include acquiring a plurality of dark images via a digital detector of an X-ray system. Acquiring the plurality of dark images may include acquiring data from a plurality of data channels of the digital detector during an analog test mode of the digital detector in which calibration voltages are applied to the data channels. The method may also include calibrating a channel gain map of the detector based on the plurality of dark images. Additional systems, methods, and devices are also disclosed.

21 Claims, 7 Drawing Sheets

GAIN CALIBRATION AND CORRECTION TECHNIQUE FOR DIGITAL IMAGING SYSTEMS

BACKGROUND

The present invention relates to digital X-ray imaging systems, and particularly to techniques for correcting gain variation in image data acquired with such systems.

A number of radiological imaging systems of various designs are known and are presently in use. Such systems generally are based upon generation of X-rays that are directed toward a subject of interest. The X-rays traverse the subject and impact a film or a digital detector. In medical diagnostic contexts, for example, such systems may be used to visualize internal tissues and diagnose patient ailments. In other contexts, parts, baggage, parcels, and other subjects may be imaged to assess their contents and for other purposes.

Increasingly, such X-ray systems use digital circuitry, such as solid-state detectors, for detecting the X-rays, which are attenuated, scattered or absorbed by the intervening structures of the subject. It will be appreciated that raw image data acquired via such X-ray systems may include a number of artifacts or other undesirable elements that may, if left uncorrected, result in visual artifacts in a reconstructed image based on the raw image data. In turn, these visual artifacts may negatively impact the ability of a user or computer to discern finer details in the image. For example, non-uniformity of various aspects of the X-ray system, such as the X-ray beam, diodes and/or data channels of a digital detector, and the like, may result in gain variation in the acquired raw image data. While certain approaches to correcting image data for such gain variation may be known, these approaches are often time-consuming and resource-intensive, and may not account for certain factors that could impact gain variation. There is a need, therefore, for improved approaches to gain calibration and correction for digital imaging systems.

BRIEF DESCRIPTION

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Some embodiments of the present invention may generally relate to techniques for correcting gain variation in image data acquired via a digital X-ray imaging system and for calibrating such systems for gain correction. In some embodiments, a method may include obtaining dark images with additive channel input voltage from a digital detector of the system and using these dark images, and in some cases only these dark images, to calibrate channel gain. Channel gain correction maps stored in the system may be used to correct acquired image data. In some embodiments, at least a portion of the gain correction of the image data is performed in the digital detector. Additional gain correction may also occur outside the digital detector in such embodiments. In other embodiments, all of the gain correction may be performed external to the digital detector. In an additional embodiment, channel gain correction maps may be updated in real-time between patient examinations to account for changes in temperature or other environmental factors.

Various refinements of the features noted above may exist in relation to various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the presently disclosed subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed subject matter, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
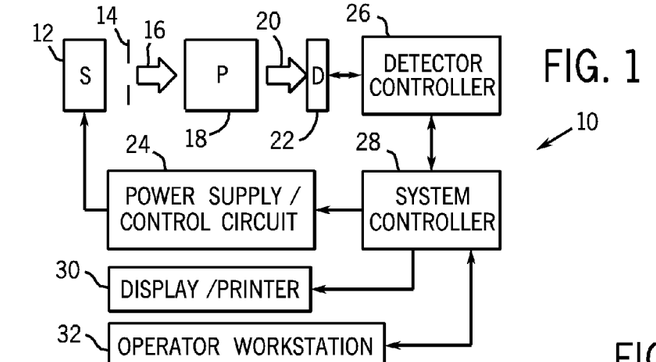
FIG. 1 is a diagrammatical overview of a digital X-ray imaging system in which the present technique may be utilized.

Turning now to the drawings, FIG. 1 illustrates diagrammatically an imaging system 10 for acquiring and processing discrete pixel image data. In the illustrated embodiment, system 10 is a digital X-ray system designed both to acquire original image data and to process the image data for display in accordance with the present technique. In the embodiment illustrated in FIG. 1, imaging system 10 includes a source of X-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital X-ray detector, represented generally at reference numeral 22. As described more fully below, detector 22 converts the X-ray photons received on its surface to lower energy photons, and subsequently to electric signals, which are acquired and processed to reconstruct an image of the features within the subject.

Source 12 is controlled by a power supply/control circuit 24 which furnishes both power and control signals for examination sequences. Moreover, detector 22 is coupled to a detector controller 26 which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
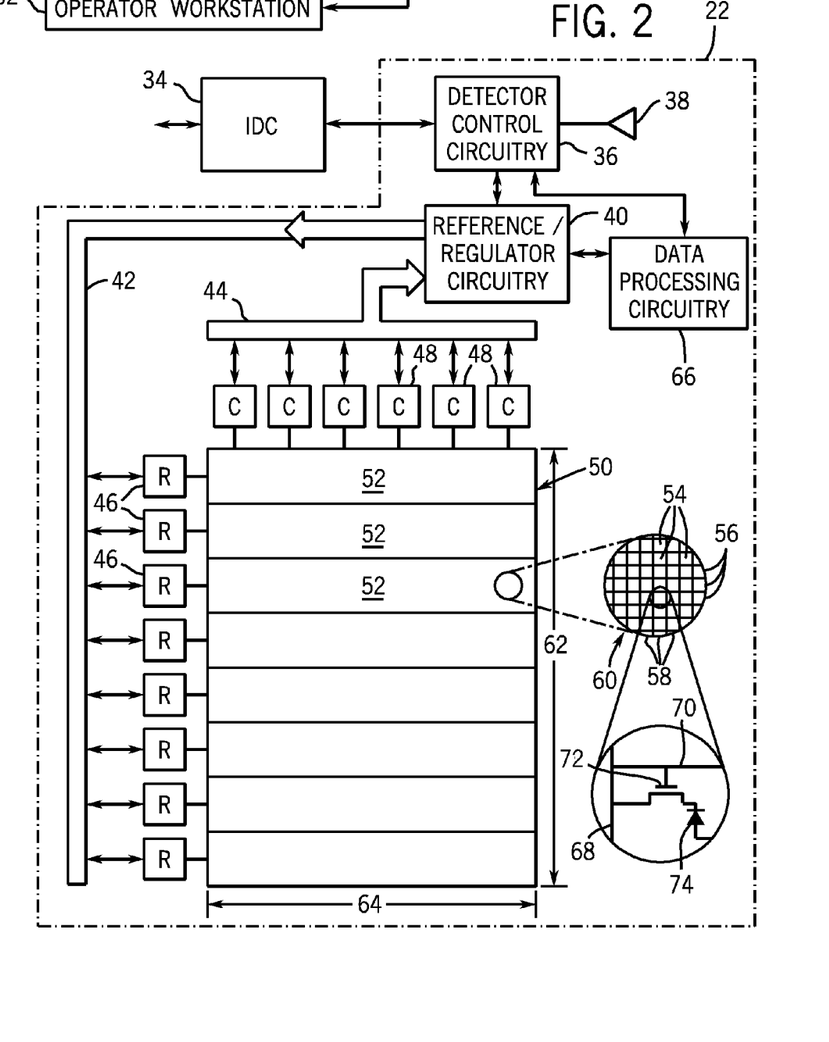
FIG. 2 is a diagrammatical representation of the functional circuitry in a detector of the system of FIG. 1 to produce image data for reconstruction.

FIG. 2 is a diagrammatical representation of functional components of digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. In certain presently contemplated embodiments, other communications systems and technologies may be used, such as Ethernet communications protocols, and wireless communications devices and protocols. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column electronics used to acquire image data during data acquisition phases of operation of the system. Circuitry 36 therefore transmits power and control signals to reference/regulator circuitry 40, and receives digital image pixel data from circuitry 40.

In a present embodiment, detector 22 consists of a scintillator that converts X-ray photons received on the detector surface during examinations to lower energy (light) photons. An array of photodetectors then converts the light photons to electrical signals which are representative of the number of photons or the intensity of radiation impacting individual pixel regions of the detector surface. In certain presently contemplated embodiments, the X-ray photons may be directly converted to electrical signals. Readout electronics convert the resulting analog signals to digital values that can be processed, stored, and displayed, such as in a display 30 or a workstation 32 following reconstruction of the image. In a present form, the array of photodetectors is formed of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and the electrode of each column is connected to an individual data channel of the readout electronics.

In the particular embodiment illustrated in FIG. 2, by way of example, a row bus 42 includes a plurality of conductors for enabling readout from various rows of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50, which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode (or data line) 68 crosses a row electrode (or scan line) 70. As mentioned above, a thin film transistor 72 is provided at each crossing location for each pixel, as is a photodiode 74. As each row is enabled by row drivers 46, signals from each photodiode 74 may be accessed via readout electronics 48, and converted to digital signals for subsequent processing and image reconstruction. Thus, an entire row of pixels in the array is controlled simultaneously when the scan line 70 attached to the gates of all the transistors of pixels on that row is activated. Consequently, each of the pixels in that particular row is connected to a data line 68, through a switch, which is used by the readout electronics to restore the charge to the photodiode 74 and measure an amount of charge depletion resulting from irradiation.

It should be noted that in certain systems, as the charge is restored to all the pixels in a row simultaneously by each of the associated dedicated readout channels, the readout electronics is converting the measurements from the previous row from an analog voltage to a digital value. Furthermore, the readout electronics may transfer the digital values from rows previous to the acquisition subsystem, which will perform some processing prior to displaying a diagnostic image on a monitor or writing it to film. In at least some embodiments, the digital detector 22 may include data processing circuitry 66 configured to perform some local processing of the data acquired via the detector panel 50 within the digital detector itself. For instance, as discussed in greater detail below, the digital detector 22 may be configured to apply channel gain correction to the acquired data independent of a host processing system, such as the system controller 28. Additionally, in one embodiment, the digital detector 22 may apply such correction to the acquired data before outputting the data to other components of the system 10.

The circuitry used to enable the rows may be referred to in a present context as row enable or field effect transistor (FET) circuitry based upon the use of field effect transistors for such enablement (row driving). The FETs associated with the row enable circuitry described above are placed in an "on" or conducting state for enabling the rows, and are turned "off" or placed in a non-conducting state when the rows are not enabled for readout. Despite such language, it should be noted that the particular circuit components used for the row drivers and column readout electronics may vary, and the present invention is not limited to the use of FETs or any particular circuit components.

Figure 3:
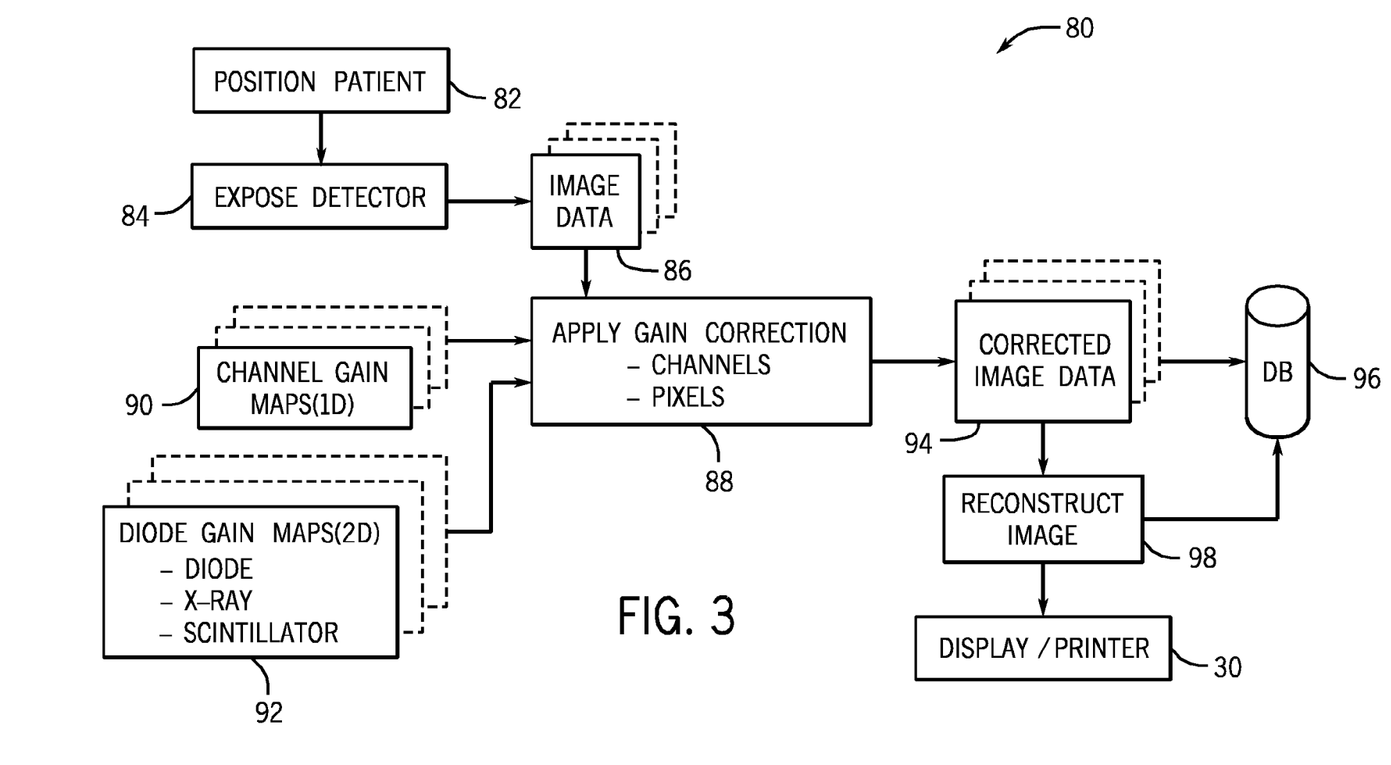
FIG. 3 generally illustrates an imaging process that includes applying gain correction of digital image data via one-dimensional and two-dimensional gain maps in accordance with one embodiment.

An example of an imaging workflow of the system 10 of FIG. 1 is generally illustrated as diagram 80 in FIG. 3 in accordance with one embodiment. While the present workflow is generally described with respect to a medical context, in which image data is acquired regarding a patient, it will be appreciated that the presently disclosed techniques may also find use in non-medical contexts. In one embodiment, the patient 18 may be positioned with respect to the radiation source 12 and the digital detector 22 to facilitate imaging of a patient anatomy, as generally indicated in block 82.

Once the patient is positioned, the detector 22 may be exposed, as generally indicated by block 84, to generate image data 86 representative of the patient anatomy. It is noted that the raw image data 86 may include a number of artifacts or other undesirable elements, and may generally be subjected to various filtering, correction, and/or other processing techniques to, for example, reduce artifacts and enhance the image data. One such technique may include a gain correction technique, as generally illustrated at block 88.

As may be appreciated, each of the photodiodes 74 of the digital detector 22, and the data channels corresponding to the data lines 68 of the digital detectors, may exhibit variations in gain relative to the other photodiodes and data channels. This non-uniformity may result in undesirable artifacts in the raw image data acquired from the detector panel 50. Additionally, X-rays from the radiation source 12 may impact the detector panel 50 in a non-uniform manner, and a scintillator of the digital detector may also include non-uniformities, which may lead to additional artifacts in the raw image data.

In one embodiment, however, the system 10 may, in a step 88, use one or more gain correction maps to correct for such gain variations in the raw image data 86. Such gain maps may include, for example, one or more channel gain maps 90 and/or diode gain maps 92. Generally, a diode gain map 92 includes a two-dimensional matrix of factors by which the output signals of the pixels may be modified. For instance, in a 2048 pixel×2048 pixel digital detector, the diode gain map may include a corresponding 2048×2048 matrix of coefficients for correcting signals from the pixels to compensate for pixel non-uniformity. The diode gain maps 92 may include separate gain correction maps for diode non-uniformity, X-ray non-uniformity, or scintillator non-uniformity, for instance. Further, in some embodiments, the diode gain maps 92 may include one or more composite gain correction maps, in which the correction coefficients account for two or more of the above-noted pixel non-uniformities. It is also noted that the extent of non-uniformity of the diodes, the scintillator, and the X-ray beam may vary with respect to different X-ray spectra related to different X-ray filters and different peak kilovoltage (kVp) levels applied to the source 12 (e.g., an X-ray tube). Consequently, in one embodiment, the diode gain maps 92 may include various gain correction maps for different filters and/or for different kVp levels. For example, a particular system 10 may be configured to apply multiple distinct kVp levels, or a range of kVp levels (e.g., 40 kVp-120 kVp), to an X-ray tube. In such an embodiment, the diode gain maps 92 may include one or more gain correction maps for each of the distinct kVp levels, or for representative kVp levels within the range (e.g., 60 kVp, 80 kVp, and 120 kVp, in one embodiment).

Conversely, as the data channels of the detector 22 correspond to the data lines 68, and as each data line is coupled to a column of pixels 54, in some embodiments a channel gain map 90 may include a one-dimensional matrix (e.g., a 1×2048 matrix) of factors that may each be applied to signals from a respective data channel to correct for gain non-uniformity of the data channels. The non-uniformity of the data channels may vary in proportion to the sensitivity level selected for a particular application. For example, in one embodiment, the system 10 may be used for both radiographic and fluoroscopic image acquisition. For radiographic applications, the sensitivity level of the system 10 may be set at one or more levels, such as 2200 electrons per count (in which case the system equates 2200 detected electrons with one digital unit) or 4400 electrons per count. For fluoroscopic applications, however, the sensitivity level may be only 550 electrons per count or 1100 electrons per count. In such an embodiment, the channel gain maps 90 may include four channel gain correction maps—one for each sensitivity level of the system. It is noted that although the channel gain maps 90 and diode gain maps 92 are distinct from one another in at least some embodiments, these maps could be combined in other embodiments (e.g., forming a two-dimensional combined gain map by multiplying each column of the diode map with the corresponding channel map).

The raw image data 86 may be corrected through the above techniques, as well as any other desired techniques, resulting in corrected image data 94. This corrected image data 94 may be stored in a database 96, such as a memory device of an electronic system. In a step 98, the corrected image data 94 may be used to reconstruct one or more images of the patient anatomy. The reconstructed image may be output to the database 96 for storage, and may be output to a healthcare professional or other user, such as via a display or printer.

Figure 4:
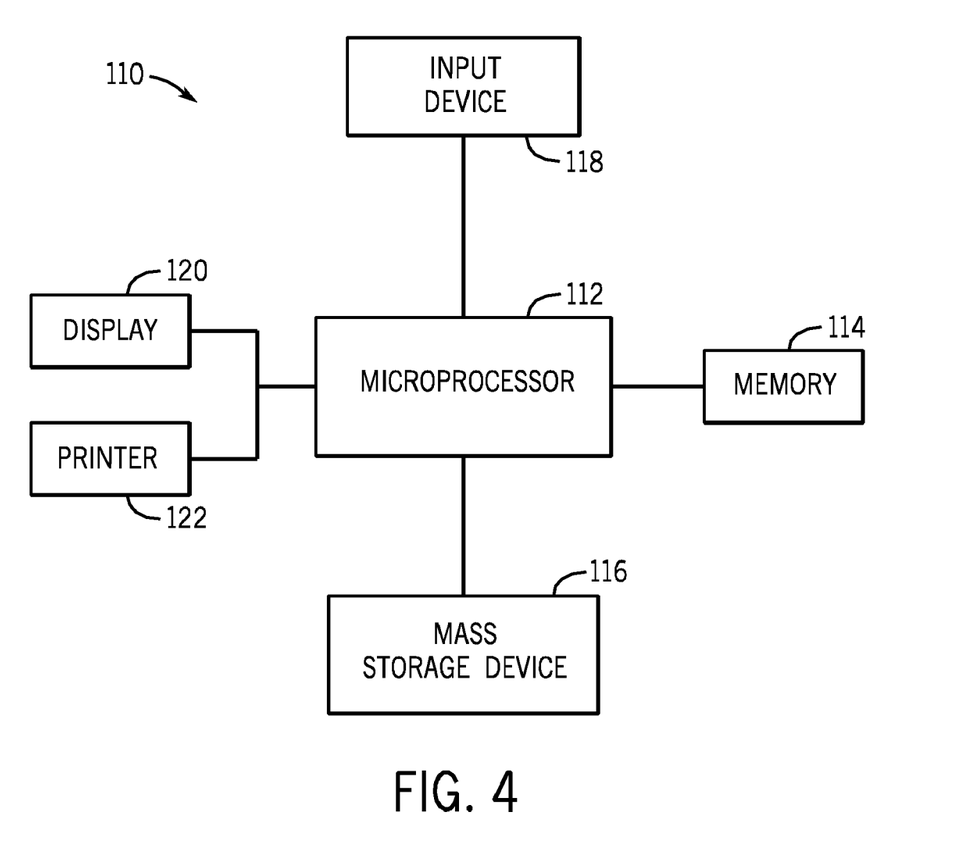
FIG. 4 is a block diagram of a processor-based device or system that may be configured to implement functionality described herein in accordance with one embodiment.

Various functionality, including image data gain correction and calibration of the detector 22 described herein, may be performed by, or in conjunction with, a processor-based system 110, which is generally depicted in FIG. 4 in accordance with one embodiment. For example, the various controllers and circuitry discussed herein may include, or be partially or entirely embodied in, a processor-based system, such as that presently illustrated. The exemplary processor-based system 110 may be a general-purpose computer, such as a personal computer, configured to run a variety of software, including software implementing all or part of the functionality described herein. Alternatively, in other embodiments, the processor-based system 110 may include, among other things, a distributed computing system, or an application-specific computer or workstation configured to implement all or part of the presently described functionality based on specialized software and/or hardware provided as part of the system. Further, the processor-based system 110 may include either a single processor or a plurality of processors to facilitate implementation of the presently disclosed functionality.

In one embodiment, the exemplary processor-based system 110 includes a microcontroller or microprocessor 112, such as a central processing unit (CPU), which executes various routines and processing functions of the system 110. For example, the microprocessor 112 may execute various operating system instructions, as well as software routines configured to effect certain processes, stored in or provided by a manufacture including one or more computer readable-media (at least collectively storing the software routines), such as a memory 114 (e.g., a random access memory (RAM) of a personal computer) or one or more mass storage devices 116 (e.g., an internal or external hard drive, a solid-state storage device, a CD-ROM, a DVD, or another storage device). In addition, the microprocessor 112 processes data provided as inputs for various routines or software programs, such as data provided as part of the present subject matter described herein in computer-based implementations.

Such data may be stored in, or provided by, the memory 114 or mass storage device 116. Alternatively, such data may be provided to the microprocessor 112 via one or more input devices 118. The input devices 118 may include manual input devices, such as a keyboard, a mouse, or the like. In addition, the input devices 118 may include a network device, such as a wired or wireless Ethernet card, a wireless network adapter, or any of various ports or devices configured to facilitate communication with other devices via any suitable communications network, such as a local area network or the Internet. Through such a network device, the system 110 may exchange data and communicate with other networked electronic systems, whether proximate to or remote from the system 110.

Results generated by the microprocessor 112, such as the results obtained by processing data in accordance with one or more stored routines, may be provided to an operator via one or more output devices, such as a display 120 and/or a printer 122. Based on the displayed or printed output, an operator may request additional or alternative processing or provide additional or alternative data, such as via the input device 118. Communication between the various components of the processor-based system 110 may typically be accomplished via a chip set and one or more busses or interconnects which electrically connect the components of the system 110. In one embodiment, the exemplary processor-based system 110 can be configured to, among other things, receive image data, apply gain correction to the image data via one or more gain correction maps, and output the corrected image data.

As generally noted above, the pixels 54 of the digital detector 22 produce analog voltage signals in response to X-rays impinging the detector panel 50. These analog signals are then converted to digital values by the detector 22, which may then be output to other components of the system 10, such as the system controller 28. In one embodiment, rather than sampling the analog signals in one single stage to determine the signal level, the analog signals are sampled through multiple stages to reduce the amount of time required for the analog to digital conversion.

Figure 5:
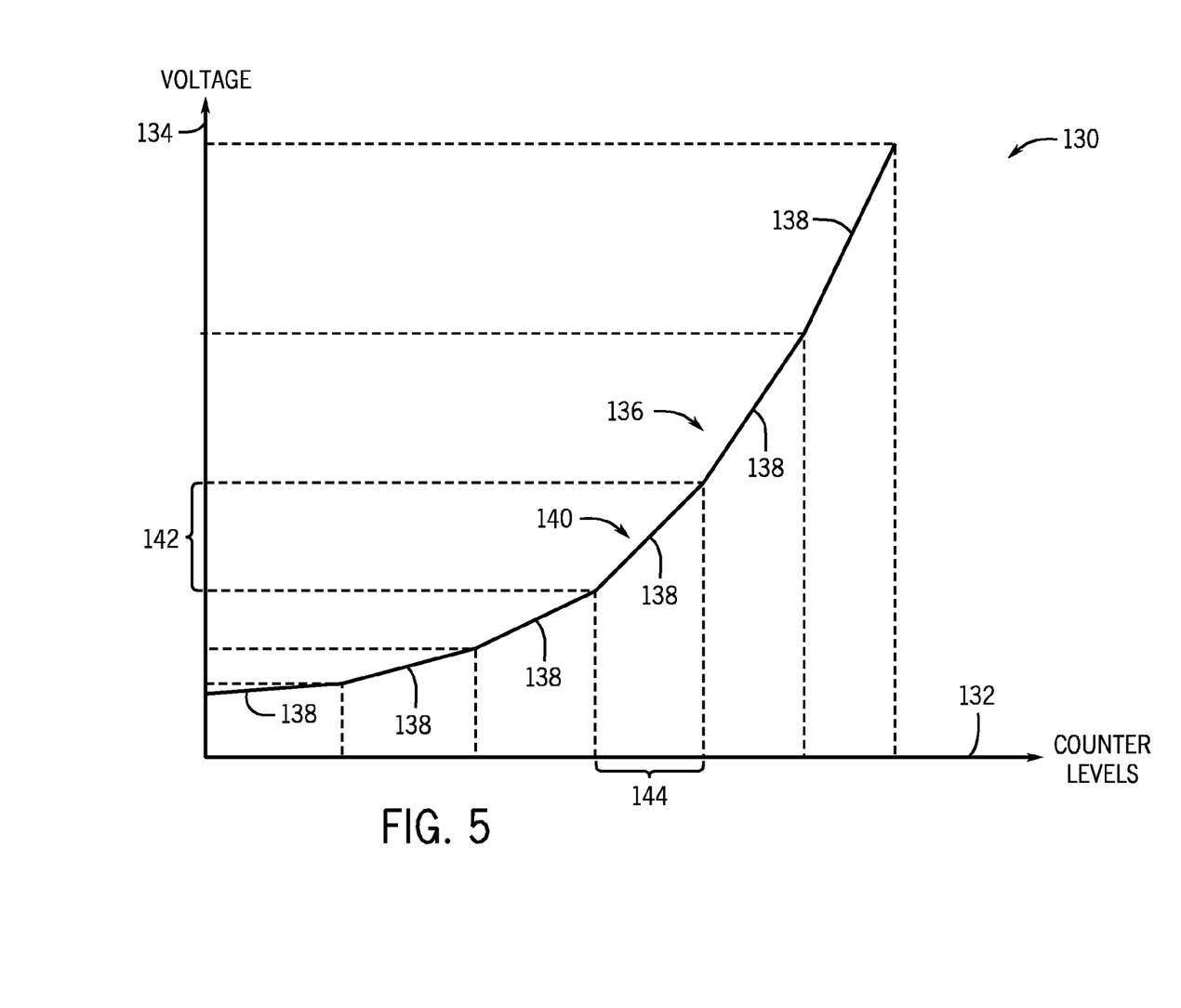
FIG. 5 illustrates a graph generally representative of a two-stage sampling process that may be used in the conversion of analog data of a digital X-ray detector to digital data in accordance with one embodiment.

One example of a conversion process using two sampling stages may be better understood with reference to FIG. 5. Particularly, the depicted graph 130 includes a curve 136 generally representative of a conversion level counter or an index of conversion levels (along horizontal axis 132) corresponding to an analog voltage level (along vertical axis 134). In one embodiment, the possible range of analog signals and corresponding counter levels may be divided into multiple segments 138, and an analog signal may undergo coarse sampling to determine the particular segment 138 (corresponding to sub-ranges of both voltage and counter levels) to which the signal belongs. Subsequently, the analog signal may undergo fine sampling within that segment 138 to determine its magnitude and a corresponding digital value. For instance, the coarse sampling may determine that a signal is within a particular segment 140, which corresponds to a voltage range 142 and a counter level range of 144. The signal may then be sampled within the segment 140 (e.g., compared to various discrete voltage levels within the voltage range 142) to determine the voltage of the signal and an associated counter level (a digital value). In one embodiment, the sub-ranges for the various segments 138 may be selected to minimize the actual numbers of conversion levels for the given ratio of quantization noise to X-ray quantum noise and signal dynamic range.

In one embodiment, for fine sampling, the segments 138 (or ramps) may be adjusted by a programmable gain to match the required resolution. For instance, each segment 138 (or ramp) may have a slope adjusted by a programmable gain $G'^{\{k\}}$. This programmable gain, however, could be varied from channel to channel. As a result, the sampled and decoded data could be affected by the variation of the gain applied to the ramp. Additionally, while the segments 138 are presently depicted as line segments for the sake of explanation, it is noted that the segments 138 (and the correspondence between voltage and digital signal that they represent) may be non-linear in other embodiments.

Figure 6:
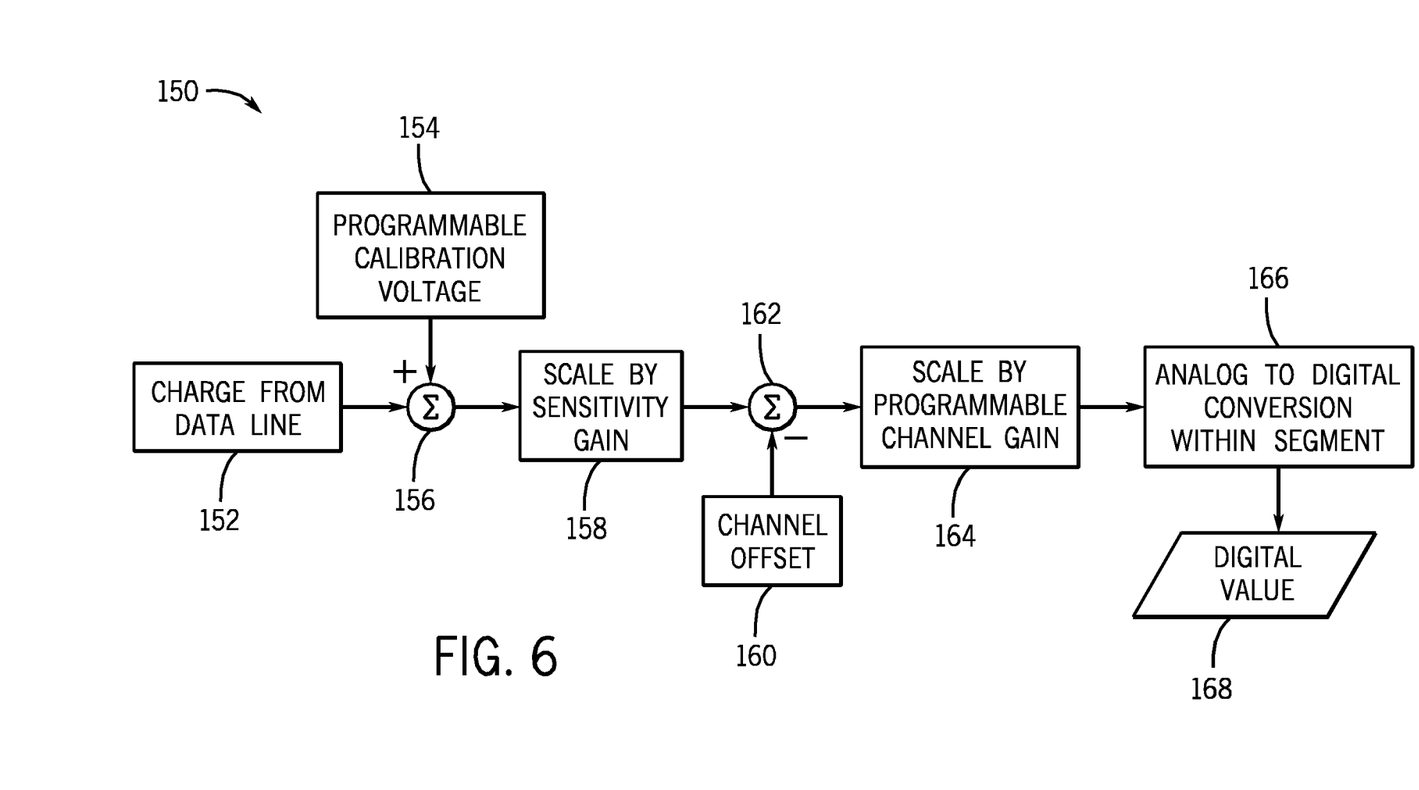
FIG. 6 is a diagrammatical representation of the conversion of analog data from the digital X-ray detector to digital data in accordance with one embodiment.

A block diagram 150 further representative of calibration of an analog to digital conversion process in accordance with one embodiment is depicted in FIG. 6. In one embodiment, the data channels of the digital detector 22 include an analog test mode. In this mode, each data line 68 is connected to a diode through a thin film transistor, and the charge from the data line 68 is generally represented in block 152 of the diagram. An analog voltage source in the digital detector 22 is configured to provide a calibration voltage ($V_{cal}$), represented generally at reference numeral 154. In one embodiment, the input of a detector data channel is the sum of the charge from the associated data line 68 and the calibration voltage, as generally indicated at reference numeral 156. This signal may be amplified, as generally represented at reference numeral 158, by a sensitivity gain, $G_{\{s\}}(j)$, where $s=0, 1, \ldots, S-1$, with S being the number of sensitivity levels of the system 10, and $j=0, 1, \ldots, J-1$, with J being the number of channels of the system 10.

As generally represented by reference numerals 160 and 162, respectively, the signal may undergo coarse sampling, equivalent to offset subtraction, where the offset is $O^{\{k\}}(j)$; $k=0, 1, \ldots, K-1$; and K is the number of different segments 136 discussed above. In some embodiments K may equal 0 or 1, while in other embodiments K may equal a higher number (e.g., 16) to enable faster analog to digital conversion, as generally discussed above. The signal may subsequently be scaled by a programmable channel gain $G^{\{k\}}(j)$, where $G^{\{k\}}(j)=1/G'^{\{k\}}(j)$, as generally represented at reference numeral 164. Further, as generally indicated at reference numeral 166, the scaled signal may then undergo fine sampling within a segment 136 to determine a digital value 168 representative of the signal.

By way of further example, a calibration process in accordance with the present techniques is provided below, in which c(i, j) represents the charge of the photodiode 74 located at row i and column j of the image matrix 60 and a calibration voltage $V_{cal}$ is applied to the data line 68. When read from the row i, c(i, j) may be summed with $V_{cal}$, scaled by sensitivity gain, $G_{\{s\}}(j)$, offset by $O^{\{k\}}(j)$, and amplified by channel programmable gain $G^{\{k\}}(j)$, in which case the output signal $S_{Vcal}(i,j,s,k)$ of the data channel on column j of the detector may be represented as:

$$S_{Vcal}(i,j,s,k) = G^{\{k\}}(j) \times \{G_{\{s\}}(j) \times [c(i,j) + V_{cal}] - O^{\{k\}}(j)\}, \quad (1)$$

where i=0, 1, . . . , I−1, j=0, 1, . . . , J−1, s=0, 1, . . . ,S−1, k=0, 1, . . . , K−1.

For each sensitivity level, s, and segment, k, two dark images (i.e., images acquired when the detector 22 is not exposed to radiation from source 12) corresponding to $V_{cal}$=x and $V_{cal}$=y may be acquired, such that:

$$S_x(i,j,s,k) = G^{\{k\}}(j) \times \{G_{\{s\}}(j) \times [c(i,j)+x] - O^{\{k\}}(j)\} \quad (2)$$

and $$S_y(i,j,s,k) = G^{\{k\}}(j) \times \{G_{\{s\}}(j) \times [c(i,j)+y] - O^{\{k\}}(j)\}. \quad (3)$$

Subtracting Equation (3) from (2) yields:

$$S_x(i,j,s,k) - S_y(i,j,s,k) = G^{\{k\}}(j) \times G_{\{s\}}(j) \times [x-y], \quad (4)$$

which gives the channel gain and channel offset by:

$$G^{\{s,k\}}(j) = G^{\{k\}}(j) \times G_{\{s\}}(j) = \frac{S_x(i,j,s,k) - S_y(i,j,s,k)}{x-y} \quad (5)$$

$G_{\{s\}}(j)$ and $G^{\{k\}}(j)$ may be separated by estimating $G^{\{s,k\}}(j)$ at different s or k with nominal value at $G^{\{0\}}(j)=1$. The offset could further be estimated by:

$$O^{\{k\}}(j) = G_{\{s\}}(j) \times [c(i,j)+y] - S_y(i,j,s,k)/G^{\{k\}}(j). \quad (6)$$

A more robust gain and offset estimate could also be determined by using a whole image:

$$G^{\{s,k\}}(j) = \frac{1}{I}\sum_{i=0}^{I-1} \frac{S_x(i,j,s,k) - S_y(i,j,s,k)}{x-y}, \quad (7)$$
$$j = 0, \ldots, J-1, s = 0, \ldots, S-1, k = 0, \ldots, K-1$$

and $$O^{\{k\}}(j) = \frac{1}{I}\sum_{i=0}^{I-1} \{G_{\{s\}}(j) \times [c(i,j)+y] - S_y(i,j,s,k)/G^{\{k\}}(j)\}, \quad (8)$$
$$j = 0, \ldots, J-1, s = 0, \ldots, S-1, k = 0, \ldots, K-1$$

The above approach can be used to obtain channel gains for all S sensitivity levels that are selected in the applications and segment gains used for ramp slope. In some embodiments, because the channel gain calibration only requires dark images with various input $V_{cal}$ levels, this calibration can be performed by the system 10 in the background between patient examinations or during detector quality assurance procedures to save calibration time.

It is noted that $G_{\{s\}}(j)$ and $G^{\{k\}}(j)$ are independent, and only (S+2×K) sets of dark images could be used to determine the individual gain. The sensitivity and programmable channel gains may also be combined, and (S×2×K) data sets could be used for the calibration. Careful selection of $V_{cal}$ around the two cross points of each segment k, however, may enable the system to use (K+1) dark images to estimate gain, $G^{\{k\}}(j)$, and offset, $O^{\{k\}}(j)$. In such an embodiment, as few as (S+K+1) dark images could be used for channel gain calibration.

In one embodiment, channel gain correction may be applied in the digital detector 22, itself, so that all image data received at the host (e.g., the system controller 28) will have already been corrected for channel gain. If $\overline{G}^{\{s,k\}}$ is the mean of the J channel gains at programmable gain k, then:

$$\overline{G}^{\{s,k\}} = \frac{1}{J}\sum_{j=0}^{J-1} G^{\{s,k\}}(j) = \frac{1}{J}\sum_{j=0}^{J-1} G_{\{s\}}(j) \times G^{\{k\}}(j) \quad (9)$$

and $$G_C^{\{s,k\}}(j) = \overline{G}^{\{s,k\}}/G^{\{s,k\}}(j), \quad (10)$$
$$j = 0, 1, \ldots, J-1, k = 0, 1, \ldots, K-1, s = 0, 1, \ldots, S-1$$

All image pixels {p(i, j)}, values of which are located in segment k, may then be corrected:

$$\hat{p}(i,j) = G_C^{\{s,k\}}(j) \times [p(i,j) + O^{\{k\}}(j)/G^{\{k\}}(j)], i = 0,1,\ldots,I-1; j=0,1,\ldots,J-1 \quad (11)$$

where $G_C^{(s,k)}(j)$ is previously stored values from calibration and k, $G^{\{k\}}(j)$, and $O^{\{k\}}(j)$ are determined by sampling the panel readout signal before it is compensated by channel gain and offset. Channel gain corrected image pixel {$\hat{p}(i, j)$} may then be output from the detector 22, such as to the system controller 26.

In one embodiment, the channel gain maps 90 may be automatically calibrated while the system 10 is idle or during a detector quality assurance procedure, and an appropriate channel gain map 90 may be selected to correct acquired image data based on the system sensitivity level selected for a given image acquisition procedure. In one embodiment, all images or image data received by the host will have channel gain corrected by Equation (11) in the detector 22. The host, for example the system controller 26, may then apply additional correction, including, but not limited to, gain correction for non-uniformity of the photodiodes 74, scintillator, and X-ray beam for different kVp levels and beam filters.

In another embodiment, however, the channel gain correction may be performed outside of the digital detector 22, such as by the system controller 26. In such an embodiment, once the channel gain and channel offset are obtained, the gain of the diode $D_{kVp}(i, j)$ may be calibrated at one or more of the detector sensitivity levels. If $G_{kVp}^{\{s,k\}}(i, j)$ represents the overall detector gain obtained at sensitivity level s, gain segment k, and a particular kVp level, then:

$$G_{kVp}^{\{s,k\}}(i,j) = G_C^{\{s,k\}}(j) \times D_{kVp}(i,j) \quad (12)$$

Further, the diode gain map at a particular kVp level may be represented by:

$$D_{kvp}(i, j) = \frac{G_{kVp}^{\{s,k\}}(i, j)}{G_C^{\{s,k\}}(j)}. \quad (13)$$

In such an embodiment, the system may be able to provide gain correction for the non-uniformities discussed above, while only storing the channel gain for each of the sensitivity levels and segments, and the diode gain for each of the kVp levels. Consequently, the memory space required for storing the gain correction maps may be significantly reduced. For instance, if calibrating the digital detector 22 for three different kVp levels, four sensitivity levels, and five programmable channel gain and channel offset levels, the memory space for the new gains may be represented by $((3\times I\times J)+(2\times 4\times 5\times J))$ words, rather than $((3\times 4\times 5\times I\times J)+(4\times 5\times J))$ words. In an embodiment having only one programmable channel gain with zero channel offset, however, the memory space for the new gains are only $(3\times I\times J)+(4\times J)$ words instead of $(3\times 4\times I\times J)$ words—a memory space savings of approximately three-fourths. Additionally, with the number of gain maps reduced by three-fourths, the gain calibration time through the present techniques may similarly be reduced by approximately three-fourths.

It is noted that the discussion above assumed that each column of the image matrix 60 is readout from the same data channel. In other embodiments, however, the detector 22 may include a split panel, in which the top half and bottom halves of an image are read out from two different data modules (i.e., the top half of each column is read out from one channel and the bottom half is read out from a different channel). In such embodiments, the approach described above may still be applied with simple modifications that would be apparent to those of ordinary skill in the art in view of the present disclosure.

Figure 7:
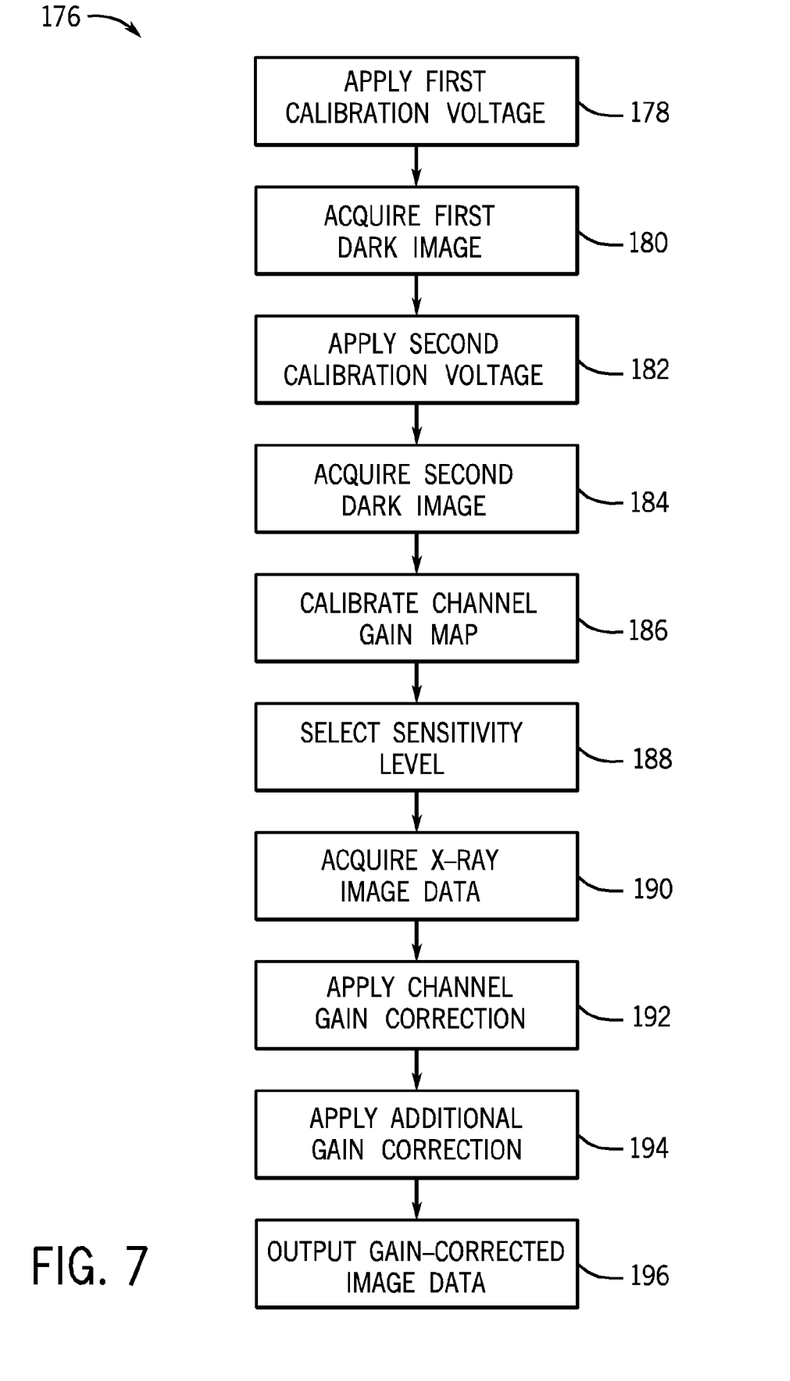
FIG. 7 is a flowchart of a process for operating a digital X-ray imaging system in accordance with one embodiment.
Figure 8:
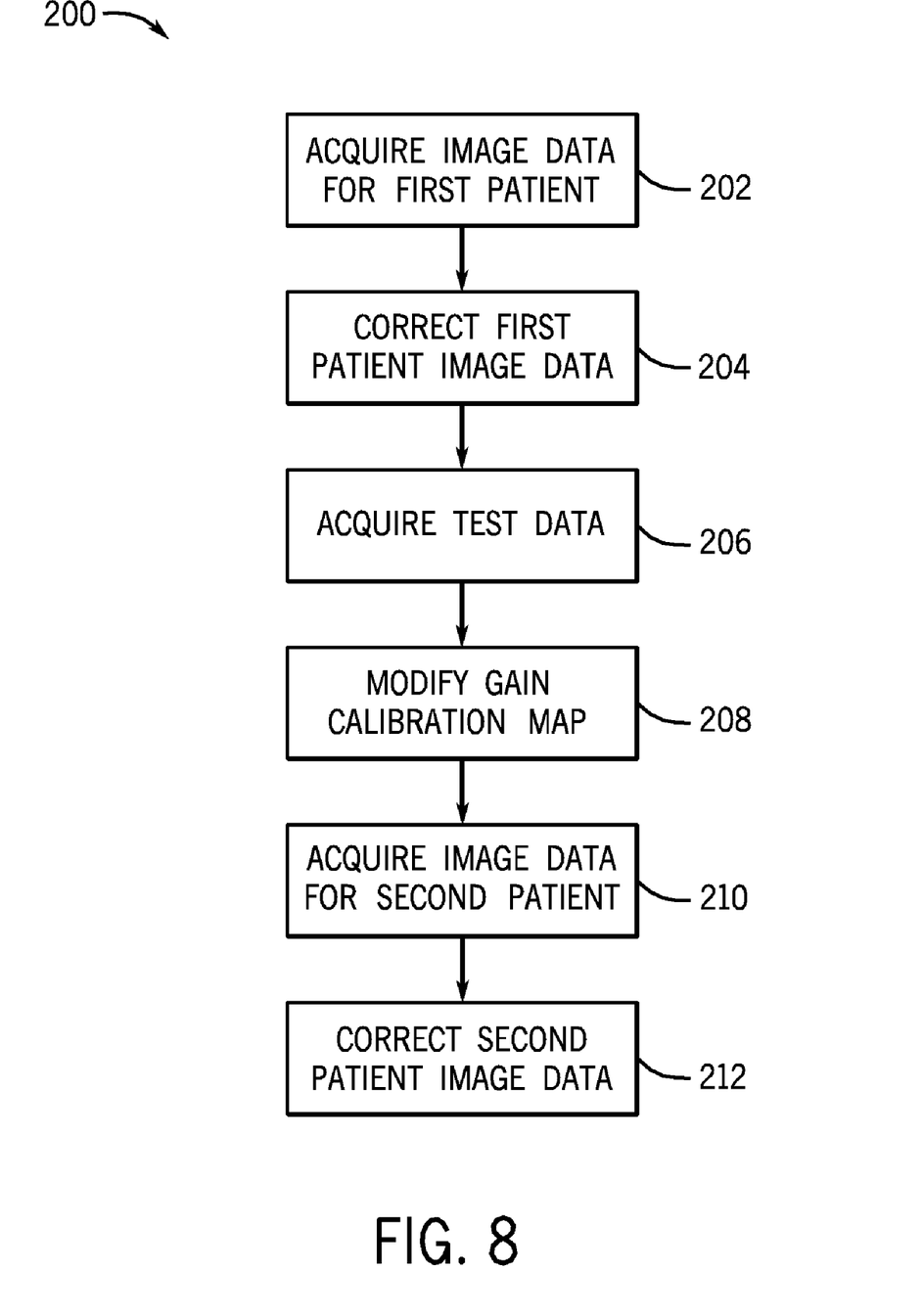
FIG. 8 is a flowchart of another process for operating a digital X-ray system in accordance with one embodiment.

Examples of methods of calibrating a digital X-ray system and acquiring image data in accordance with the above-referenced techniques are generally illustrated in FIGS. 7 and 8. Referring first FIG. 7, a method 176 may include a step 178 of applying a first calibration voltage to one or more data lines 68 of the detector 22 and, in a step 180, acquiring a dark image from the detector 22. As generally noted above, a dark image generally corresponds to the acquisition of data from the data channels of the detector 22 during a period of non-exposure by the radiation source 12. Such dark images may be acquired between patient imaging sessions, or during idle times between detector exposures. In a step 182, a second calibration voltage may be applied to the data lines 68, and an additional dark image may be acquired in a step 184. A channel gain map stored in the system 10 may then be calibrated in a step 186 based on the dark image data acquired in step 180 and 184, as discussed in greater detail above.

In a step 188, a sensitivity level for the system 10 may be selected. The sensitivity level may be selected by the system 10 automatically and/or may be selected by the system 10 in response to a user input, such as a technician input to the system 10. The detector 22 may subsequently be exposed by the radiation source 12 to acquire X-ray image data in a step 190. The system 10 may also apply channel gain correction in a step 192 based on the calibrated channel gain map, as discussed above. In one embodiment, the sensitivity level selection may be used to select one of a number of different channel gain correction maps, which may be used to apply channel gain correction to the acquired X-ray image data.

Additionally, in a step 194, further gain correction or other forms of correction may be applied to the image data. The corrected image data may then be output in a step 196.

In FIG. 8, an additional method 200 may include a first acquisition process generally including a step 202 of acquiring image data from a first patient via the system 10, and correcting the acquired data, in a step 204, as generally discussed above. The method 200 may also include a calibration process of acquiring test data, such as dark images during an analog test mode of the detector 22, in a step 206, and modifying one or more gain calibration maps (e.g., a channel gain calibration map) in a step 208. Additionally, the method 200 may include a second image acquisition process generally corresponding to the illustrated steps 210 and 212 of acquiring image data from a second patient and correcting the acquired image data with the calibrated gain map, respectively. In at least some embodiments, the calibration process may be automatically executed by the system 10 between the first and second imaging processes, and may generally facilitate the updating of gain calibration maps in real-time to account for variation in temperature or other environmental factors.

Technical effects of the invention include the ability to calibrate channel gain maps using only dark image data obtained during a test mode, and the ability to automatically calibrate channel gain maps during system idle periods to account for environmental impact. Additionally, channel gain correction may be performed in the detector itself, reducing processing loads on the system host. Still further, memory space and calibration time requirements are believed to be greatly reduced in comparison to the current state of the art.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method comprising:
    acquiring a plurality of dark images via a digital detector of an X-ray system, wherein acquiring the plurality of dark images includes acquiring data from a plurality of data channels of the digital detector during an analog test mode of the digital detector in which calibration voltages are applied to the data channels; and
    calibrating a channel gain map of the detector based on the plurality of dark images.

2. The method of claim 1, wherein calibrating the channel gain map is based solely on the plurality of dark images.

3. The method of claim 1, wherein calibrating the channel gain map is performed independent of any image generated by irradiating the digital detector with a radiation source of the X-ray system.

4. The method of claim 1, wherein calibrating the channel gain map includes determining respective channel gain levels for the data channels.

5. The method of claim 4, wherein acquiring the plurality of dark images includes:
    acquiring a first dark image at a first calibration voltage; and
    acquiring a second dark image at a second calibration voltage different from the first calibration voltage.

6. The method of claim 5, wherein determining respective channel gain levels includes determining a ratio of a difference of output signal voltages of at least one data channel at the respective first and second calibration voltages to a difference between the first and second calibration voltages.

7. The method of claim 1, comprising:
acquiring X-ray image data via the digital detector; and
correcting the X-ray image data based on the calibrated channel gain map.

8. The method of claim 7, wherein correcting the X-ray image data includes correcting the X-ray image data within the digital detector.

9. The method of claim 8, comprising:
outputting the channel gain corrected X-ray image data from the digital detector; and
correcting the X-ray image data based on one or more additional gain maps.

10. The method of claim 1, wherein the X-ray system includes a medical X-ray system, and wherein calibrating the channel gain map is performed automatically between patient imaging sessions with the X-ray system such that the channel gain map calibration accounts for environmental factors variable from one patient imaging session to another.

11. A computer-implemented method comprising:
using a digital X-ray system to:
execute a first imaging process via the digital X-ray system, the first imaging process including:
exposing a digital image detector of the digital X-ray system to X-ray radiation to generate first image data; and
correcting the first image data based on a gain correction map stored in a memory device of the digital X-ray system, wherein correcting the first image data based on a gain correction map includes correcting the first image data based on:
a two-dimensional gain map configured to account for non-uniformity of at least one of:
diodes of the digital image detector;
an x-ray beam generated by the digital X-ray system; or
a scintillator of the digital image detector; and
a one-dimensional gain map configured to account for non-uniformity of data channels in the digital image detector;
execute a gain calibration process including:
acquiring test data from the digital image detector; and
modifying the gain correction map based on the acquired test data; and
execute a second imaging process via the digital X-ray system, the second imaging process including:
exposing the digital image detector of the digital X-ray system to X-ray radiation to generate second image data; and
correcting the second image data based on the modified gain correction map.

12. The method of claim 11, wherein using the digital X-ray system to execute a gain calibration process includes using the digital X-ray system to automatically execute the gain calibration process between the first and second imaging processes.

13. The method of claim 11, comprising using the digital X-ray system to electronically store at least one of the corrected first image data or the corrected second image data in the memory device of the X-ray system or in an additional memory device.

14. The method of claim 11, comprising reconstructing one or more images based on at least one of the corrected first image data or the corrected second image data.

15. An imaging system comprising:
an x-ray radiation source;
a digital detector configured to generate image data;
control circuitry configured to acquire the image data from the digital detector; and
processing circuitry configured to apply gain correction to the image data via one or more gain correction maps, wherein the processing circuitry is further configured to calibrate at least one gain correction map based on a series of dark images acquired from the digital detector between exposures by the x-ray radiation source during an analog test mode of the digital detector in which calibration voltages are applied to a plurality of data channels of the digital detector.

16. The imaging system of claim 15, wherein the at least one gain correction map includes a channel gain correction map stored in a memory device.

17. The imaging system of claim 16, wherein the digital detector includes the memory device and at least a portion of the processing circuitry, and is configured to apply channel gain correction to the image data via the channel gain map.

18. The imaging system of claim 17, wherein the digital detector is configured to output the channel gain-corrected image data to an additional portion of the processing circuitry external to the digital detector, the additional portion of the processing circuitry configured to apply additional gain correction to the channel gain-corrected image data.

19. The imaging system of claim 16, wherein the memory device and at least a portion of the processing circuitry are external to the digital detector, and the imaging system is configured to apply channel gain correction to the image data via the channel gain map external to the digital detector.

20. The imaging system of claim 15, wherein the imaging system includes a portable imaging system.

21. A manufacture comprising:
a non-transitory computer-readable storage medium having executable application instructions stored thereon, wherein the application instructions include:
instructions adapted to receive test data acquired from a plurality of data channels of a digital image detector during a test mode in which the digital image detector is not being used to acquire image data of an object of interest and in which calibration voltages are applied to the data channels; and
instructions adapted to calibrate a channel gain map based on the test data, the channel gain map representative of gain correction to be applied to image data acquired through exposure of the digital image detector to an X-ray source of an imaging system.

* * * * *